United States Patent [19]

Lucien

[11] Patent Number: 4,542,248

[45] Date of Patent: Sep. 17, 1985

[54] PROCESS FOR THE PREPARATION OF A $C_2$–$C_4$ PARAFFIN DEHYDROGENATION CATALYST

[75] Inventor: Jacques P. Lucien, Amsterdam, Netherlands

[73] Assignee: Shell Oil Company, Houston, Tex.

[21] Appl. No.: 597,946

[22] Filed: Apr. 9, 1984

Related U.S. Application Data

[62] Division of Ser. No. 504,930, Jun. 16, 1983, Pat. No. 4,469,811.

[30] Foreign Application Priority Data

Jul. 1, 1982 [NL] Netherlands ............ 8202647

[51] Int. Cl.$^4$ ............ C07C 3/03; C07C 5/40; B01J 21/04
[52] U.S. Cl. ............ 585/322; 585/315; 585/415; 585/417; 585/660; 585/661
[58] Field of Search ............ 585/322, 315, 415, 417, 585/660, 661; 502/227, 230, 326, 352

[56] References Cited

U.S. PATENT DOCUMENTS

| | | | |
|---|---|---|---|
| 3,531,543 | 9/1970 | Clippinger et al. | 585/660 |
| 3,641,182 | 2/1972 | Box, Jr. et al. | 585/660 |
| 3,674,706 | 7/1972 | Box, Jr. et al. | 585/660 |
| 3,760,024 | 9/1973 | Cattanach | 585/415 |
| 3,845,150 | 10/1974 | Yan et al. | 585/415 |
| 3,851,003 | 11/1974 | Wilhelm | 585/660 |
| 4,438,287 | 3/1984 | Imai | 585/660 |
| 4,469,811 | 9/1984 | Lucien | 585/660 |

FOREIGN PATENT DOCUMENTS

1275830  5/1972  United Kingdom ............ 585/660

Primary Examiner—D. E. Gantz
Assistant Examiner—A. Pal

[57] ABSTRACT

A process is described wherein $C_2$–$C_4$ paraffins are dehydrogenated over a catalyst which has been prepared by (a) impregnating an $Al_2O_3$ carrier with an aqueous solution of a Sn-compound;
(b) calcining the impregnated carrier;
(c) impregnating the composition with an aqueous solution of a Pt-compound;
(d) reducing the composition;
(e) removing at least part of any halogen introduced in step (a) and/or (c) by treating the composition with a non-acidic solution comprising $NH_4^+$ ions until the halogen content of the final catalyst amounts to less than 0.1% w; and
(f) impregnating the composition with a non-acidic (halogen-free) aqueous solution of an alkali metal compound.

The $C_2$–$C_4$-olefins formed are converted to aromatic gasoline over a catalyst containing a crystalline metal silicate having a ZSM-5 structure.

11 Claims, No Drawings

PROCESS FOR THE PREPARATION OF A $C_2$-$C_4$ PARAFFIN DEHYDROGENATION CATALYST

This is a division of application Ser. No. 504,930, filed June 16, 1983, now U.S. Pat. No. 4,469,811.

BACKGROUND OF THE INVENTION

The invention relates to a process for the preparation of a catalyst suitable for the dehydrogenation of paraffins with two, three or four carbon atoms per molecule.

Olefins with two, three or four carbon atoms per molecule can be converted into $C_5+$ aromatic hydrocarbon mixtures in high yields at relatively low temperatures by contacting the olefins with a crystalline metal silicate having a special structure as catalyst. Said crystalline metal silicates are characterized in that, after one hour's calcination in air at 500° C., they have the following characteristics:
(a) thermally stable up to a temperature of at least 600° C.,
(b) an X-ray powder diffraction pattern in which the strongest lines are the four lines mentioned in Table A.

TABLE A

| d(Å) |
| --- |
| 11.1 ± 0.2 |
| 10.0 ± 0.2 |
| 3.84 ± 0.07 |
| 3.72 ± 0.06 |

(c) in the formula which represents the composition of the silicate expressed in moles of the oxides and which, in addition to $SiO_2$, includes one or more oxides of a trivalent metal A, chosen from the group formed by aluminum, iron, gallium and chromium, the $SiO_2/A_2O_3$ molar ratio is higher than 10.

In this patent application a crystalline silicate having a thermal stability of at least 600° C. should be taken to be a silicate whose X-ray powder diffraction pattern remains substantially unchanged upon heating to a temperature of 600° C.

Converting paraffins with two, three or four carbon atoms per molecule (for the sake of brevity hereinafter referred to as "$C_2$-$C_4$ paraffins") in the same way is much harder and requires considerably higher temperatures, resulting in a substantial degree of cracking and low yields of $C_5+$ hydrocarbons. A solution to this problem may be found in a two-stage process in which the paraffins are partly converted into olefins by dehydrogenation, whereupon in a second stage these olefins are converted over the silicate catalyst. Since the second stage of this process is carried out at a relatively low temperature at which only olefins formed in the first stage are converted and no further dehydrogenation of paraffins occurs, it is an optimum course of the first stage on which the success of the process largely depends. A decisive part is played in this respect by the performance of the catalyst used in the first stage. In addition to the catalyst's activity and selectivity to olefins, its stability is of particularly great importance, since the first stage is carried out at a high temperature and in the presence of olefins, which favors polymerization reactions and coke formation.

The present patent application is based on the results of an investigation into the use as catalysts for the dehydrogenation of $C_2$-$C_4$ paraffins of alkali metal promoted compositions which include the metal combination platinum/tin supported on alumina as a carrier. At first these catalyst were prepared in the conventional manner by impregnation of an alumina carrier by using aqueous solutions of $SnCl_2$ and $H_2PtCl_6$ as impregnation liquors. In view of the highly unsatisfactory results obtained when using these chlorine-containing catalysts for the dehydrogenation of $C_2$-$C_4$ paraffins an evaluation was made of the possibilities of improving on these results by using catalysts which had been prepared by the above-described conventional method, but whose chlorine content had been reduced by a steam treatment to less than 0.1% w in the final catalyst and also by using substantially chlorine-free catalysts by carrying out the preparation using aqueous solutions of sodium stannate and tetramine platinum hydroxide as impregnation liquors. Although these catalysts showed a somewhat better performance in the dehydrogenation of $C_2$-$C_4$ paraffins, their stability was still far too low for use on a technical scale.

It is known to prepare $Pt/Sn/Al_2O_3$ dehydrogenation catalysts containing alkali metal or alkaline earth metal promoters by the methods described in U.S. Pat. No. 3,998,900.

SUMMARY OF THE INVENTION

It has not been found that alkali metal promoted compositions which comprise the metal combination platinum/tin supported on alumina as the carrier and which show excellent stability when used as catalysts for the dehydrogenation of $C_2$-$C_4$ paraffins, can be prepared by using impregnation liquors in which the platinum and/or tin compound occurs in the form of a halogen-containing compound as follows:
(a) impregnating an alumina carrier with an aqueous solution of a tin compound;
(b) calcining the composition;
(c) impregnating the composition with an aqueous solution of a platinum compound;
(d) reducing the composition;
(e) removing at least part of the halogen ions, which were introduced into the composition by using a halogen-containing platinum compound and/or tin compound in steps (a) and/or (c), by treating the composition with a non-acidic aqueous solution comprising $NH_4+$ ions to provide a final catalyst containing less than 0.1% w of halogen; and
(f) impregnating the composition with a non-acidic aqueous solution of an alkali metal compound.

DETAILED DESCRIPTION OF THE INVENTION

The present patent application therefore relates to a process for the preparation of an alkali metal promoted catalyst comprising the metal combination platinum/tin supported on alumina as the carrier, which preparation is carried out in the manner described hereinbefore under (a) and (f) inclusive. The application further relates to the use of such catalysts for the conversion of hydrocarbons, in particular for the dehydrogenation of $C_2$-$C_4$ paraffins. Finally, the application relates to a two-stage process for the preparation of a $C_5+$ aromatic hydrocarbon mixture from $C_2$-$C_4$ paraffins, in which the paraffins are dehydrogenated in the first stage over an alkali metal promoted Pt/Sn on alumina catalyst prepared according to the invention and in which the reaction product from the first stage is subjected in the second stage to aromatization by using one of the crystalline metal silicates described hereinbefore as catalyst.

In the catalyst preparation according to the invention an alumina carrier is first impregnated with an aqueous solution of a tin compound and after calcination of the tin-containing composition the latter is impregnated with an aqueous solution of a platinum compound. In the impregnation liquors used at least one of the metal compounds should occur as a halogen-containing compound. If desired, both a halogen-containing tin compound and a halogen-containing platinum compound may be used. An example of a halogen-containing tin compound very suitable for the present purpose is tin chloride. Examples of suitable halogen-free tin compounds are tin acetate, tin tartrate and sodium stannate. The impregnation with the tin compound is preferably carried out in such a manner that a catalyst is obtained which contains 0.1–2.0 and in particular 0.1–1.0 pbw of tin per 100 pbw of alumina. After impregnation with the tin compound, the composition is preferably dried before being subjected to calcination. An example of a halogen-containing platinum compound very suitable for the present purpose is $H_2PtCl_6$.

An example of a suitable halogen free platinum compound is platinum tetramine hydroxide. Impregnation with the platinum compound is preferably carried out in such a manner that a catalyst is obtained which contains 0.05–2.0 and in particular 0.1–1.0 pbw of platinum per 100 pbw of alumina. After impregnation with the platinum compound the composition is preferably dried before being subjected to reduction. Reduction of the tin and platinum-containing composition is preferably carried out at a temperature of 400°–600° C. using hydrogen as reducing agent. In order to remove at least part of the halogen ions which were introduced into the composition during impregnation with the tin compound and/or platinum compound, the reduced composition is treated with a non-acidic solution comprising $NH_4^+$-ions. The treatment is carried out in such a manner that the final catalyst contains less than 0.10% w of halogen.

In the treatment with the aqueous solution comprising $NH_4^+$-ions treatment time, treatment temperature and concentration of the solution may vary within wide limits. In general, more halogen is removed as the treatment is carried out at a higher temperature and over a longer period using a solution of higher concentration. As non-acidic solutions comprising $NH_4^+$-ions may be carried out under very mild conditions. Treatment at room temperature for 10 minutes using a solution of 5% of ammonia in water may produce the desired result. If desired, the treatment may be repeated once or several times, each time using a fresh solution.

After the $NH_4^+$-treatment the composition is preferably dried before being subject to impregnation with a non-acidic aqueous solution of an alkali metal compound. The alkali metal compound used is preferably a cesium compound. Very suitable for the present purpose is cesium hydroxide. The impregnation with the alkali metal compound is preferably carried out in such a manner that it yields a catalyst which contains 0.05–10 and in particular 0.1–3.0 pbw of alkali metal per 100 pbw of alumina.

Catalysts prepared according to the invention may, among other things, be used for the conversion of hydrocarbons. They are excellently suitable for the dehydrogenation of $C_2$–$C_4$ paraffins, in particular for the dehydrogenation of propane, n-butane and isobutane and mixtures thereof. The paraffins to be hydrogenated preferably contain less than 25% w ethane. A very suitable feed is a hydrocarbon mixture which consists substantially of $C_3$ and $C_4$ paraffins and which has been obtained as a by-product in the production of crude mineral oil.

The dehydrogenation is preferably carried out at a temperature of 400°–650° C. and in particular of 500°–600° C., a pressure of 0.1–10 bar and in particular of 0.5–3 bar and a space velocity of 1–20 kg.kg$^{-1}$.h$^{-1}$ and in particular of 2–10 kg.kg$^{-1}$.h$^{-1}$. During the dehydrogenation it is preferred to add hydrogen to the feed, since this has been found to enchance the stability of the catalyst to a considerable extent. Before being contacted with the feed the catalyst is preferably subjected to a hydrotreatment carried out at an elevated temperature. A catalyst according the the invention which is very suitable for carrying out the dehydrogenation of $C_2$–$C_4$ paraffins is a catalyst containing 0.2–0.4 pbw of platinum, 0.3–0.5 pbw of tin and 0.2–2.5 pbw of alkali metal per 100 pbw of alumina.

As stated hereinbefore, the present patent application also relates to a two-stage process for the preparation of a $C_5^+$ aromatic hydrocarbon mixture from $C_2$–$C_4$ paraffins, in which the paraffins are dehydrogenated in the first stage over a catalyst prepared according to the invention and in which the reaction product from the first step is subjected in a second step to aromatization by using a crystalline metal silicate having a special structure as catalyst. Said crystalline metal silicates are defined, among other things, by their X-ray powder diffraction pattern. In this pattern the strongest lines should be the four lines mentioned in Table A. The complete X-ray powder diffraction pattern of a typical example of a silicate applicable in the two-stage process is given in Table B.

TABLE B

| d(Å) | Rel. Int. | d(Å) | Rel. Int. |
|---|---|---|---|
| 11.1 | 57 | 3.84 (D) | 100 |
| 10.0 (D) | 31 | 3.72 (D) | 70 |
| 8.93 | 1 | 3.63 | 16 |
| 7.99 | 1 | 3.47 | 1 |
| 7.42 | 2 | 3.43 | 5 |
| 6.68 | 7 | 3.34 | 2 |
| 6.35 | 11 | 3.30 | 5 |
| 5.97 | 17 | 3.25 | 1 |
| 5.70 | 7 | 3.05 | 8 |
| 5.56 | 10 | 2.98 | 11 |
| 5.35 | 2 | 2.96 | 3 |
| 4.98 (D) | 6 | 2.86 | 2 |
| 4.60 | 4 | 2.73 | 2 |
| 4.35 | 5 | 2.60 | 2 |
| 4.25 | 7 | 2.48 | 3 |
| 4.07 | 2 | 2.40 | 2 |
| 4.00 | 4 | | |

(D) = doublet

The crystalline metal silicates may be prepared starting from an aqueous mixture which comprises the following compounds: one or more compounds of an alkali metal (M), one or more organic nitrogen compounds (RN) which include an organic cation or from which an organic cation is formed during the preparation of the silicate, one or more silicon compounds, one or more compounds in which a trivalent metal A occurs.

The preparation is carried out by maintaining the mixture at an elevated temperature until the silicate has formed and subsequently separating the silicate crystals from the mother liquor and washing, drying and calcining the crystals. In the aqueous mixture from which the silicates are prepared the various compounds should be present in the following molar ratios expressed—with the exception of the organic nitrogen compounds—in moles of the oxides:
$M_2O: SiO_2 = 0.01-0.35$,
$Rn: SiO_2 = 0.02-1.0$,
$SiO_2: A_2O_3 > 10$, and
$H_2O: SiO_2 = 5-65$.

In the preparation of the silicates the base mixture may very suitably be a mixture in which the organic nitrogen compound present is a quaternary alkylammonium compound, such as a tetrapropylammonium compound. Preferably the organic nitrogen compound used is an amine and in particular n-butylamine. In the preparation of the silicates it is further preferred to start from a base mixture in which the alkali metal compound used is a sodium compound and the silicon compound used is amorphous silica.

The silicates prepared in the above-described manner contain metal ions. By using suitable exchange methods the latter may be replaced by other cations, such as hydrogen ions or ammonium ions. The crystalline silicates which are used as catalysts preferably have an alkali metal content of less than 0.05% w.

The crystalline silicates used as catalysts in the second stage of the two-stage process may comprise either one or several trivalent metals A. Preference is given to the use of a crystalline silicate comprising both iron and aluminum. The aromatization is preferably carried out at a temperature of 200°-500° C. and in particular of 300°-450° C., a pressure of 0.1-20 bar and in particular of 0.5-10 bar and a space velocity of 0.5-10 kg.kg$^{-1}$.h$^{-1}$ and in particular of 1-5 kg.kg$^{-1}$.h$^{-1}$. The $C_4^-$ fraction of the product obtained in the aromatization in addition to hydrogen and methane includes $C_2$-$C_4$ paraffins and olefins. In order to increase the yield of $C_5^+$ product at least part of the $C_4^-$ product and in particular the $C_3$-$C_4$ fraction thereof should preferably be recycled to the first stage.

The invention is now illustrated with the aid of the following example.

EXAMPLE

Eight alkali metal promoted catalysts (catalysts 1-8) comprising the metal combination platinum/tin supported on alumina as carrier were used for the dehydrogenation of $C_3$-$C_4$ paraffins.

Catalyst 1

The catalyst was prepared by impregnation of an alumina carrier with aqueous solutions of $SnCl_2$, $H_2PtCl_6$ and CsOH. The catalyst contained 1.0 pbw platinum, 0.4 pbw tin, 2.0 pbw cesium and 1.0 pbw chlorine per 100 pbw alumina.

Catalyst 2

This catalyst was prepared by impregnation of an alumina carrier with aqueous solutions of sodium stannate, platinumtetramine hydroxide and cesium hydroxide. The catalyst contained 1.0 pbw platinum, 0.4 pbw tin and 2.0 pbw cesium per 100 pbw alumina.

Catalyst 3

This catalyst was prepared by a sequence of impregnation of an alumina carrier with an aqueous solution of $SnCl_2$, drying at 100° C., calcination for 1 hour at 500° C., impregnation with an aqueous solution of $H_2PtCl_6$, drying at 100° C., calcination for 1 hour at 400° C., treatment for 2 hours at 400° C. with air containing 20%v steam, impregnation with an aqueous solution of CsOH and drying at 100° C. The catalyst contained 1.0 pbw platinum, 0.4 pbw tin and 2.0 pbw cesium per 100 pbw alumina and had a chlorine content of less than 0.1% w.

Catalyst 4

This catalyst was prepared by a sequence of impregnation of an alumina carrier with an aqueous solution of $SnCl_2$, drying at 100° C., calcination for 1 hour at 500° C., impregnation with an aqueous solution of $H_2PtCl_6$, drying at 100° C., reduction with hydrogen for 1 hour at 500° C., treatment with an aqueous solution containing 10% w ammonia for 10 minutes at room temperature, drying at 100° C., impregnation with an aqueous solution of CsOH and drying at 100° C. The catalyst contained 1.0 pbw platinum 0.4 pbw tin and 2.0 pbw cesium per 100 pbw alumina and had a chlorine content of less than 0.05% w.

Catalyst 5

This catalyst was prepared in the same manner as catalyst 4. The catalyst contained 0.3 pbw platinum, 0.4 pbw tin and 2.0 pbw cesium per 100 pbw alumina and had a chlorine content of less than 0.05% w.

Catalyst 6

This catalyst was prepared in substantially the same manner as catalyst 4, with the distinction that in the present instance the impregnation with an aqueous solution of CsOH was replaced by impregnation with an aqueous solution of NaOH. The catalyst contained 1.0 pbw platinum, 0.4 pbw tin and 0.5 pbw sodium per 100 pbw alumina and had a chlorine content of less than 0.05% w.

Catalyst 7

This catalyst was prepared in the same manner as catalyst 4. The catalyst contained 0.5 pbw platinum, 0.4 pbw tin and 2.0 pbw cesium per 100 pbw alumina and had a chlorine content of less than 0.05% w.

Catalyst 8

This catalyst was prepared in the same manner as catalyst 4. The catalyst contained 0.15 pbw platinum, 0.4 pbw tin and 2.0 pbw cesium per 100 pbw alumina and had a chlorine content of less than 0.05% w.

Catalyst 9

A second stage catalyst was prepared by heating a mixture of NaOH, Fe(NO$_3$)$_3$, NaAlO$_2$, amorphous silica containing 100 ppmw aluminum, and C$_4$H$_9$NH$_2$, in water, which mixture had the molar composition 1 Na$_2$O.10 C$_4$N$_9$NH$_2$.0.036 Al$_2$O$_3$.0.020 Fe$_2$O$_3$.25 SiO$_2$.450 H$_2$O in an autoclave under autogeneous pressure and with stirring for 24 hours at 150° C. After cooling of the reaction mixture the silicate formed was filtered off, washed with water until the pH of the wash water was about 8 and dried at 120° C. After one hour's calcination in air at 500° C. the silicate had the following properties:
(a) thermally stable up to a temperature of at least 800° C.,
(b) an X-ray powder diffraction pattern substantially corresponding with that mentioned in Table B, and (c) a $SiO_2/Fe_2O_3$ molar ratio of 127 and a $SiO_2/Al_2O_3$ molar ratio of 600.

The silicate thus obtained was used to prepare catalyst 9 by boiling the silicate with a 1.0 molar $NH_4NO_3$ solution, washing with water, boiling again with a 1.0 molar $NH_4NO_3$ solution and washing, drying at 120° C. and calcining at 500° C.

Of the Pt/Sn catalysts described above catalysts 4–8 are catalysts according to the invention. They have been included in the patent application for comparison.

Dehydrogenation experiments

Catalysts 1–6 were tested in six experiments (Experiments 1–6) for the dehydrogenation of isobutane.

Catalysts 4, 5, 7 and 8 were also tested in six experiments (Experiments 7–12) for the dehydrogenation of n-butane. In experiments 8 and 9 carried out using catalyst 4 hydrogen was added to the feed.

Experiments 1–12 were carried out in a reactor containing a fixed bed of the catalyst concerned. The experiments were carried out at a temperature of 550° C., a pressure of 1–5 bar absolute and a space velocity of 5 kg paraffin feed/kg catalyst/hour.

Finally, catalyst 4 was tested in two experiments (Experiments 13 and 14) for the dehydrogenation of $C_3$–$C_4$ paraffins in the first stage of a two-stage process for the preparation of a $C_5^+$ aromatic hydrocarbon mixture, whilst catalyst 9 was used in the second stage. Experiments 13 and 14 were carried out in two reactors containing fixed beds of the catalysts concerned. In Experiments 13 and 14 the total reaction product from the first stage was used as the feed for the second stage.

Experiment 13 was carried out using isobutane as the feed at a temperature of 550° C., a pressure of 1.5 bar absolute and a space velocity of 9.4 kg.kg$^{-1}$.hour$^{-1}$ in the first stage and at a temperature of 400° C., a pressure of 1.5 bar absolute and a space velocity of 1.6 kg.kg$^{-1}$.hour$^{-1}$ in the second stage.

Experiment 14 was carried out using propane as the feed at a temperature of 550° C., a pressure of 1.5 bar absolute and a space velocity of 5 kg.kg$^{-1}$.hour$^{-1}$ in the first stage and a temperature of 400° C., a pressure of 1.5 bar absolute and a space velocity of 2.5 kg.kg$^{-1}$.hour$^{-1}$ in the second stage.

Before being subjected to Experiments 1–14 the Pt/Sn catalysts were reduced by a one hour's hydrotreatment at 400° C.

Of Experiments 1–14 Experiments 4–14 (carried out with catalysts 4–8) are experiments according to the invention. Experiments 1–3 (carried out with catalysts 1–3) fall outside the scope of the invention. They have been included in the patent application for comparison.

The results of Experiments 1–14 are given in Tables C–F.

The results given in Tables E and F refer to the product from the second stage. The parameters activity, selectivity and stability recorded in the Tables are defined as follows:

Activity = % w paraffin feed converted.

Selectivity towards a certain component =

$$\frac{\% \text{ w component concerned present in the product}}{\% \text{ w paraffin feed converted}} \times 100.$$

Stability = decrease in activity over a given period, in % w.

TABLE C

| Experiment No. | 1 | 2 | 3 | 4 | 5 | 6 |
|---|---|---|---|---|---|---|
| Catalyst No. | 1 | 2 | 3 | 4 | 5 | 6 |
| Initial activity, % w | 40.5 | 45.0 | 41.8 | 44.8 | 44.2 | 43.6 |
| Activity averaged over 50 hours, % w | 18.4 | 29.3 | 26.8 | 37.5 | 41.1 | 32.6 |
| Stability over 50 hours, % w | 30.5 | 28.0 | 24.7 | 16.8 | 6.2 | 20.8 |
| Selectivity, averaged over 50 hours, % w | | | | | | |
| towards butenes | 89.3 | 94.6 | 95.2 | 95.3 | 95.5 | 94.8 |
| towards $H_2$ | 3.1 | 3.2 | 3.2 | 3.1 | 3.5 | 3.2 |
| towards $C_1$–$C_3$ | 5.6 | 1.3 | 1.1 | 0.8 | 1.0 | 1.2 |
| towards n-butane | 1.8 | 0.6 | 0.5 | 0.8 | 0 | 0.8 |
| towards $C_5^+$ | 0.2 | 0.2 | 0.1 | 0 | 0 | 0 |

TABLE D

| Experiment No. | 7 | 8 | 9 | 10 | 11 | 12 |
|---|---|---|---|---|---|---|
| Catalyst No. | 4 | 4 | 4 | 5 | 7 | 8 |
| $N_2$/n-butane molar ratio | — | 0.2 | 1.0 | — | — | — |
| Initial activity, % w | 43.1 | 36.8 | 32.1 | 44.2 | 42.8 | 42.1 |
| Activity averaged over 20 hours, % w | 25.4 | 36.8 | 30.6 | 37.6 | 30.2 | 22.4 |
| Stability over 20 hours, % w | 31.3 | 4.0 | 3.0 | 14.0 | 22.7 | 23.5 |
| Selectivity, averaged over 20 hours, % w towards butenes | 88.6 | 84.8 | 85.5 | 87.6 | 88.2 | 84.8 |
| towards butadiene | 4.4 | 1.4 | 1.5 | 3.1 | 3.4 | 3.7 |
| towards $H_2$ | 3.1 | 3.2 | 2.8 | 3.3 | 3.4 | 3.6 |
| towards $C_1$–$C_3$ | 3.5 | 9.4 | 7.7 | 4.8 | 3.8 | 6.2 |
| towards isobutane | 0.4 | 1.0 | 2.5 | 1.2 | 1.2 | 1.7 |
| towards $C_5^+$ | 0 | 0.1 | 0 | 0 | 0 | 0 |

TABLE E

| Experiment No. | 13 |
|---|---|
| Feed | isobutane |
| Catalyst in first stage, No. | 4 |
| Catalyst in second stage, No. | 9 |
| Activity averaged over 30 h, % w | 41.5 |
| Selectivity averaged over 30 h, % w towards $H_2$ | 3.1 |
| towards $C_1$–$C_3$ | 18.4 |
| towards n-butane | 7.7 |
| towards butenes | 7.5 |
| towards $C_5^+$ | 63.1 |
| Aromatics content $C_5^+$ product, % w | 63.5 |

TABLE F

| Experiment No. | 14 |
|---|---|
| Feed | propane |
| Catalyst in second stage, No. | 4 |
| Catalyst in second stage, No. | 9 |
| Activity averaged over 80 hours, % w | 21.0 |
| Selectivity averaged over 80 h, % w towards $H_2$ | 5.0 |
| towards $C_1$–$C_2$ | 6.2 |
| towards propene | 0 |
| towards $C_4$ hydrocarbons (olefins + paraffins) | 23.4 |
| towards $C_5^+$ | 65.4 |
| Aromatics content $C_5^+$ product, % w | 65.0 |

With reference to the results given in Tables C–F the following may be remarked.

Table C

All the catalysts display a very high initial activity. The initial yield of butenes (=the product of initial activity and selectivity towards butenes) in all instances come close to what on account of the thermodynamic equilibrium may be expected under the reaction conditions used (approximately 42% w).

Catalyst 1 (having a high chlorine content) displays a very poor performance. As a result of its poor stability the catalyst has a very low average activity. The selectivity towards butenes is too low. The catalyst shows a high degree of cracking.

Catalysts 2 and 3 (free from chlorine and having a reduced chlorine content, respectively) display a better performance than catalyst 1. As a result of their higher initial activity and better stability, they have a higher average activity. Their selectivity to butenes is higher and they show a lower degree of cracking. However, the catalysts' stability remains insufficient.

Catalyst 4 (having a reduced chlorine content and prepared according to the invention) displays a much better performance than catalysts 2 and 3, shows a very high selectivity to butenes.

Catalyst 5 has a lower platinum content than catalyst 4. This reduction of the platinum content leads to considerable improvement of the stability and thus to a further increase in average activity. The high selectivity towards butenes remains intact.

Of catalyst 6, which instead of cesium comprises sodium as promoter, stability, average activity and selectivity to butenes are good.

Table D

Comparison of the results of Experiments 7–9 shows that addition of hydrogen to the feed has a very favorable effect on the stability, which is due among other things to a lower production of butadiene. The addition of hydrogen to the feed causes the initial activity to fall, but this is due to the change in thermodynamic equilibrium which is dependent on the amount of hydrogen present. In Experiments 7–12, as in Experiments 1–6, the initial yields of butenes come very close to what on account of the thermodynamic equilibrium may be expected under the reaction conditions used.

Comparison of the results of Experiments 7, 10, 11 and 12 carried out using catalysts having differing platinum contents, shows that catalyst 5, which contains 0.3 pbw of platinum per 100 pbw of alumina clearly displays the best performance. Compared with catalysts 4, 7 and 8 (containing per 100 pbw of alumina 1.0, 0.5 and 0.15 pbw of platinum, respectively) catalyst 5 shows the best stability and thus the highest average activity.

Tables E and F

In the second stage of the process the olefins formed in the first stage are selectively converted into an aromatic $C_5^+$ hydrocarbon mixture. The $C_5^+$ product formed has a high aromatics content.

What is claimed is:

1. A process for dehydrogenating $C_2$–$C_4$ paraffins, characterized in that it comprises contacting said paraffins under dehydrogenation conditions with a dehydrogenation catalyst prepared by using impregnation liquors in which the platinum and/or tin compound occurs in the form of a halogen-containing compound as follows:
   (a) impregnating an alumina carrier with an aqueous solution of a tin compound;
   (b) calcining the composition;
   (c) impregnating the composition with an aqueous solution of a platinum compound;
   (d) reducing the composition;
   (e) removing at least part of the halogen ions, which were introduced into the composition by using a halogen-containing platinum compound and/or tin compound in steps (a) and/or (c), by treating the composition with a non-acidic aqueous solution comprising $NH_4^+$ ions to provide a final catalyst containing less than 0.1% w of halogen; and
   (f) impregnating the composition with a non-acidic aqueous solution of an alkali metal compound.

2. A process as claimed in claim 1, characterized in that the dehydrogenation is applied to $C_3$ and/or $C_4$ paraffins.

3. A process as claimed in claim 1, characterized in that the catalyst is subjected to a hydrotreatment at an elevated temperature before being contacted with the feed.

4. A process as claimed in claim 2, characterized in that hydrogen is added to the feed.

5. A process as claimed in claim 2, characterized in that it is carried out at a temperature of 400°–650° C., a pressure of 0.1–10 bar and a space velocity of 1–20 $kg.kg^{-1}.h^{-1}$.

6. A process as claimed in claim 5, characterized in that it is carried out at a temperature of 500°–600° C., a pressure of 0.5–3 bar and a space velocity of 2–10 $kg.kg^{-1}.h^{-1}$.

7. A process for the preparation of an aromatic $C_5^+$ hydrocarbon mixture from $C_2$–$C_4$ paraffins, characterized in that it is carried out in two stages, in which process the paraffins are dehydrogenated in the first stage according to a process as described in claim 1 and in which the reaction product from the first stage is aromatized in the second stage by contact under aromatizing conditions with a crystalline metal silicate as catalyst, which crystalline metal silicate after one hour's calcination in air at 500° C. has the following properties:
   (a) thermally stable up to a temperature of at least 600° C.;
   (b) an X-ray powder diffraction pattern in which the strongest lines are the four lines mentioned in Table A:

TABLE A

| d(Å) |
| --- |
| 11.1 ± 0.2 |
| 10.0 ± 0.2 |
| 3.84 ± 0.07 |
| 3.72 ± 0.06 |

(c) in the formula which represents the composition of the silicate expressed in moles of the oxides and which in addition to $SiO_2$ includes one or more oxides of a trivalent metal A chosen from the group formed by aluminum, iron, gallium and chromium, the $SiO_2/A_2O_3$ molar ratio is higher than 10.

8. A process as claimed in claim 7, characterized in that the crystalline metal silicate includes both iron and aluminum.

9. A process as claimed in claim 8, characterized in that the second stage is carried out at a temperature of 200°–500° C., a pressure of 0.1–20 bar and a space velocity of 0.5–10 $kg.kg^{-1}.h^{-1}$.

10. A process as claimed in claim 9, characterized in that the second stage is carried out at a temperature of 300°–450° C., a pressure of 0.5–10 bar and a space velocity of 1–5 $kg.kg^{-1}.h^{-1}$.

11. A process as claimed in claim 10, characterized in that at least part of the $C_4^-$ product from the second stage is recycled to the first stage.

* * * * *